(12) United States Patent
Huang

(10) Patent No.: US 11,330,979 B2
(45) Date of Patent: May 17, 2022

(54) FOCUS ADJUSTMENT METHOD AND APPARATUS

(71) Applicant: Intel Corporation, Santa Clara, CA (US)

(72) Inventor: I-Chun Huang, New Taipei (TW)

(73) Assignee: Intel Corporation, Santa Clara, CA (US)

( * ) Notice: Subject to any disclaimer, the term of this patent is extended or adjusted under 35 U.S.C. 154(b) by 273 days.

(21) Appl. No.: 16/582,578

(22) Filed: Sep. 25, 2019

(65) Prior Publication Data

US 2020/0015674 A1 Jan. 16, 2020

Related U.S. Application Data

(62) Division of application No. 15/393,687, filed on Dec. 29, 2016, now Pat. No. 10,448,824.

(51) Int. Cl.
*A61B 3/103* (2006.01)
*G02B 27/00* (2006.01)
*A61B 3/00* (2006.01)
*G02B 26/00* (2006.01)
*A61B 3/024* (2006.01)
(Continued)

(52) U.S. Cl.
CPC ............ *A61B 3/103* (2013.01); *A61B 3/0033* (2013.01); *A61B 3/024* (2013.01); *G02B 3/14* (2013.01); *G02B 26/004* (2013.01); *G02B 27/0093* (2013.01); *G02B 2027/011* (2013.01); *G02B 2027/0181* (2013.01)

(58) Field of Classification Search
CPC ....... A61B 3/103; A61B 3/0033; A61B 3/024; G02B 3/14; G02B 26/004; G02B 27/0093; G02B 2027/011; G02B 2027/0181

USPC ........................................................ 351/158
See application file for complete search history.

(56) References Cited

U.S. PATENT DOCUMENTS

2005/0254135 A1 11/2005 Ou
2014/0035959 A1* 2/2014 Lapstun ............. H04N 5/23212
345/690

(Continued)

OTHER PUBLICATIONS

International Search Report and Written Opinion, dated Feb. 1, 2018, issued in related International Application No. PCT/US2017/060455, 12 pages.

(Continued)

*Primary Examiner* — Collin X Beatty
(74) *Attorney, Agent, or Firm* — Schwabe, Williamson & Wyatt, P.C.

(57) ABSTRACT

Methods, apparatus, and system for a virtual reality device including a display monitor, an adjustable lens, and a focus sensor. The focus sensor may be used to measure a distance between an eye and the display monitor or whether the eye is able to focus images from the display monitor. The user may provide a diopter correction. The VR device may then adjust an optical power of the adjustable lens, based on at least one of the distance or whether the eye is able to focus images from the display monitor. The focus sensor may emit coded electromagnetic radiation and determine a time-of-flight of the coded electromagnetic radiation to determine the distance or whether the eye is able to focus images from the display monitor. The adjustable lens may comprise a flexible lens; the flexible lens may be adjusted with actuators, such as piezoelectric actuators.

21 Claims, 9 Drawing Sheets

(51) Int. Cl.
   *G02B 3/14*   (2006.01)
   *G02B 27/01*   (2006.01)

(56) References Cited

U.S. PATENT DOCUMENTS

| | | |
|---|---|---|
| 2016/0161740 A1* | 6/2016 | Bar-Zeev .............. G06T 19/006 |
| | | 345/633 |
| 2016/0191740 A1 | 6/2016 | Ozawa |
| 2016/0202455 A1 | 7/2016 | Aschwanden et al. |
| 2016/0270656 A1* | 9/2016 | Samec ................... A61B 3/102 |
| 2016/0278695 A1 | 9/2016 | Wang et al. |
| 2016/0320625 A1 | 11/2016 | Von Und Zu Liechtenstein |
| 2016/0370592 A1 | 12/2016 | Mak |
| 2018/0061116 A1 | 3/2018 | Mitchell et al. |
| 2021/0235054 A1* | 7/2021 | Silverstein .............. G06F 3/011 |

OTHER PUBLICATIONS

Office Action dated Jan. 10, 2019 for U.S. Appl. No. 15/393,687, 23 pages.

\* cited by examiner

FOCUS ADJUSTMENT METHOD AND APPARATUS

RELATED APPLICATION

This is a divisional application of U.S. patent application Ser. No. 15/393,687, entitled "Focus Adjustment Method and Apparatus," filed on Dec. 29, 2016, and claims priority to the Ser. No. 15/393,687 application. The Specification of Ser. No. 15/393,687 is hereby fully incorporated by reference.

FIELD

The present disclosure relates to a computer device, in particular to a device which displays images and adjusts focus.

BACKGROUND

Virtual reality ("VR") devices typically include a helmet or headset; the headset holds a display screen a fixed distance from the eyes of a person using the VR device. Some people, however, have myopia or hyperopia and need to wear glasses. Wearing glasses while wearing a VR device can be problematic, at least because glasses may not fit inside the helmet.

BRIEF DESCRIPTION OF THE DRAWINGS

Certain of the figures include dotted lines illustrating components or structures in the background, behind another component or structure. These components or structures are illustrated further in other figures; the dotted lines are not blurry or indistinct.

Figure 1:
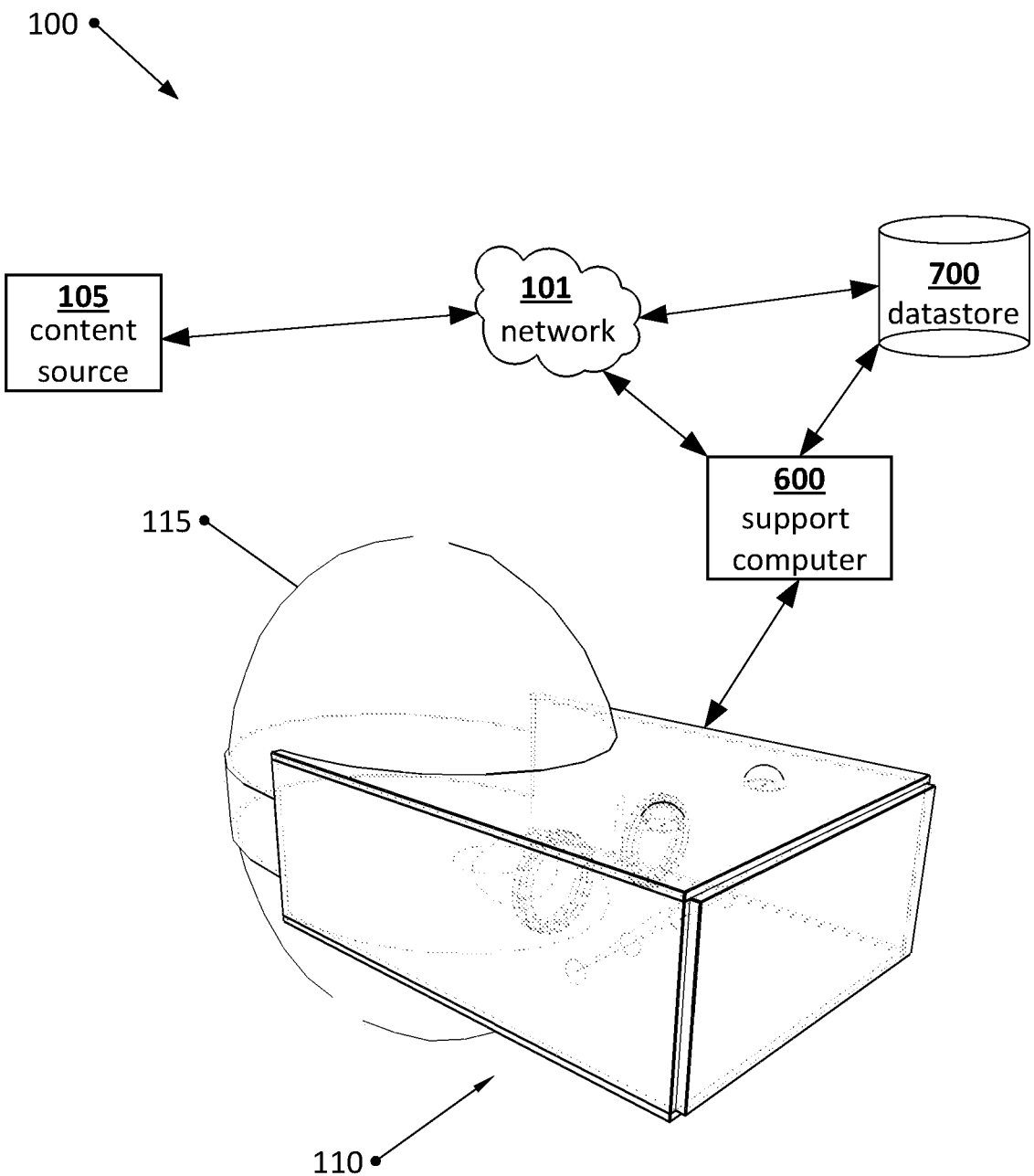
FIG. 1 is a network and device diagram illustrating an example of a VR device worn by a person in a network environment incorporated with teachings of the present disclosure, according to some embodiments.

Although the following Detailed Description will proceed with reference being made to illustrative embodiments, many alternatives, modifications, and variations thereof will be apparent to those skilled in the art.

DETAILED DESCRIPTION

Following are defined terms in this document.

As used herein, "diopter" is a reciprocal length unit of measurement of the optical power of a lens or curved mirror, equal to the reciprocal of the focal length (typically measured in meters). A "4" diopter lens brings parallel rays of light to focus at ¼ meter. Diopter is often used in the context of human vision correction to describe the correction provided by a prescription lens in a pair of glasses or a contact lens. Convex lenses have a positive dioptic value and are generally used to correct hyperopia (farsightedness) or to facilitate reading at close range. Concave lenses have negative dioptic value and generally correct myopia (nearsightedness).

As used herein, "optical power" is the degree to which a lens, mirror, or other optical system converges or diverges light. Optical power is the reciprocal of focal length.

As used herein, "focal length" is a measure of how strongly a lens, mirror, or other optical system converges or diverges light. In air, it is the distance over which initially collimated (parallel) rays are brought to a focus. A system with a shorter focal length has greater optical power compared to a system with a longer focal length.

As used in any embodiment herein, the term "logic" may refer to the logic of the instructions of an app, software, and/or firmware, and/or the logic embodied into a programmable circuitry by a configuration bit stream, to perform any of the aforementioned operations. Software may be embodied as a software package, code, instructions, instruction sets and/or data recorded on non-transitory computer readable storage medium. Firmware may be embodied as code, instructions or instruction sets and/or data that are hardcoded (e.g., nonvolatile) in memory devices.

"Circuitry", as used in any embodiment herein, may comprise, for example, singly or in any combination, hardwired circuitry, programmable circuitry such as Field Programmable Gate Arrays (FPGA). The logic may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc.

In some embodiments, a hardware description language (HDL) may be used to specify circuit and/or logic implementation(s) for the various logic and/or circuitry described herein. For example, in one embodiment the hardware description language may comply or be compatible with a very high speed integrated circuits (VHSIC) hardware description language (VHDL) that may enable semiconductor fabrication of one or more circuits and/or logic described herein. The VHDL may comply or be compatible with IEEE Standard 1076-1987, IEEE Standard 1076.2, IEEE1076.1, IEEE Draft 3.0 of VHDL-2006, IEEE Draft 4.0 of VHDL-2008 and/or other versions of the IEEE VHDL standards and/or other hardware description standards.

As used herein, the term "module" or "logic" (which, for the purposes of this disclosure, should be considered synonyms) may refer to, be part of, or include an Application Specific Integrated Circuit (ASIC), a System on a Chip (SoC), an electronic circuit, a programmed programmable circuit (such as, FPGA), a processor (shared, dedicated, or group) and/or memory (shared, dedicated, or group) or in another computer hardware component or device that execute one or more software or firmware programs having executable machine instructions (generated from an assembler and/or a compiler) or a combination, a combinational logic circuit, and/or other suitable components with logic that provide the described functionality. Modules may be distinct and independent components integrated by sharing or passing data, or modules may be subcomponents of a single module, or be split among several modules. The components may be processes running on, or implemented on, a single compute node or distributed among a plurality of compute nodes running in parallel, concurrently, sequentially or a combination, as described more fully in conjunction with the flow diagrams in the figures.

As used herein, a process corresponds to an instance of a program, e.g., an application program, executing on a processor and a thread corresponds to a portion of the process. A processor may include one or more execution core(s). The processor may be configured as one or more socket(s) that may each include one or more execution core(s).

In overview, this disclosure relates to a VR device including a display screen or display monitor, an adjustable lens, and a focus sensor. The focus sensor may be used to measure at least one of a distance between an eye and the display monitor or a diopter of an eye. The VR device may then adjust an optical power of an adjustable lens, based on at least one of the distance or the diopter. The focus sensor may emit electromagnetic radiation; time-of-flight of the electromagnetic radiation may be determined and used to determine the distance. The focus sensor may comprise a structured light sensor; the structured light sensor may comprise more than one transmitter and more than one receiver. The transmitters may emit electromagnetic radiation comprising codes; the receivers may receive the coded electromagnetic radiation, may determine the time-of-flight of the coded electromagnetic radiation, and may determine whether the electromagnet radiation is focused on a retina based on a difference among the time-of-flight of the coded electromagnetic radiation. The adjustable lens may comprise a flexible lens; the flexible lens may be ringed with actuators, such as piezoelectric actuators. The actuators may be energized to compress or expand an outer perimeter of the flexible lens, changing the optical power of the flexible lens.

In this way, people who wear glasses or people who would benefit from an adjustable optical power in a visual system in a VR device may be able to obtain such benefits, without having to wear glasses or contact lenses while wearing a VR device configured according to the disclosure herein.

FIG. 1 is a network and device diagram illustrating an example of a VR device 110 worn by a person (also referred to herein as a "user") in a network environment incorporated with teachings of the present disclosure, according to some embodiments. Head 115 of the person is illustrated in FIG. 1. FIG. 1 illustrates VR device 110 and head 115 as partially transparent, allowing a partial view of internal structures and components (illustrated in greater detail, herein).

FIG. 1 illustrates support computer 600. Support computer 600 is illustrated and discussed further in relation to FIG. 6. In embodiments, support computer 600 may be part of VR device 110, support computer 600 may be a separate component, relative to VR device 110, and/or components or parts of support computer 600 may be part of VR device 110. Support computer 600 may provide computational and memory services to VR device 110, such as, for example, network services, codec and other video and audio processing services, VR services (such as OpenGL, user-space device drivers, gesture recognition, voice recognition, compass, inertial measurement unit processing, external image processing, processing of a VR video-audio file, and the like) display driver services, and the like. In support device memory 650 illustrated in FIG. 6, modules, routines, and/or logic to provide such services is illustrated as VR services 658. In addition, support computer 600 may provide focus sensor logic, such as focus sensor logic 800, to operate one or more focus sensor(s) in VR device, as described further herein in relation to FIG. 8.

Support computer 600, except for the teachings of the present disclosure, may include, but is not limited to, a virtual reality or augmented reality display or supporting computers therefore, a server, a workstation computer, a desktop computer, a laptop computer, a tablet computer (e.g., iPad®, GalaxyTab® and the like), an ultraportable computer, an ultramobile computer, a netbook computer and/or a subnotebook computer; a mobile telephone including, but not limited to a smart phone, (e.g., iPhone®, Android®-based phone, Blackberry®, Symbian®-based phone, Palm®-based phone, etc.) and the like.

Also illustrated in FIG. 1 is datastore 700. Datastore 700 is illustrated and discussed further in relation to FIG. 7. Datastore 700 generally should be understood as a datastore used by support computer 600. Datastore 700 may be physically co-located with support computer 600 and/or may be remote therefrom.

Also illustrated in FIG. 1 is network 101. Network 101 may comprise computers, switches, routers, gateways, network connections among the computers, and software routines to enable communication between the computers over the network connections. Examples of Network 101 comprise wired networks, such as an Ethernet networks, and/or a wireless networks, such as a WiFi, GSM, TDMA, CDMA, EDGE, HSPA, LTE or other network provided by a wireless service provider; local and/or wide area; private and/or public, such as the Internet. More than one network may be involved in a communication session between the illustrated devices. Connection to Network 101 may require that the computers execute software routines which enable, for example, the seven layers of the OSI model of computer networking or equivalent in a wireless phone network.

Also illustrated in FIG. 1 is content source 105. Content source 105 may be a source of content provided to VR device 110. Content may include audio and video, including audio and video formatted to produce a virtual reality and/or augmented reality environment for a person using VR device 110. Content source 105 may have a direct connection to and/or may be a part of support computer 600 (rather than connecting via network 101, as illustrated).

Figure 2:
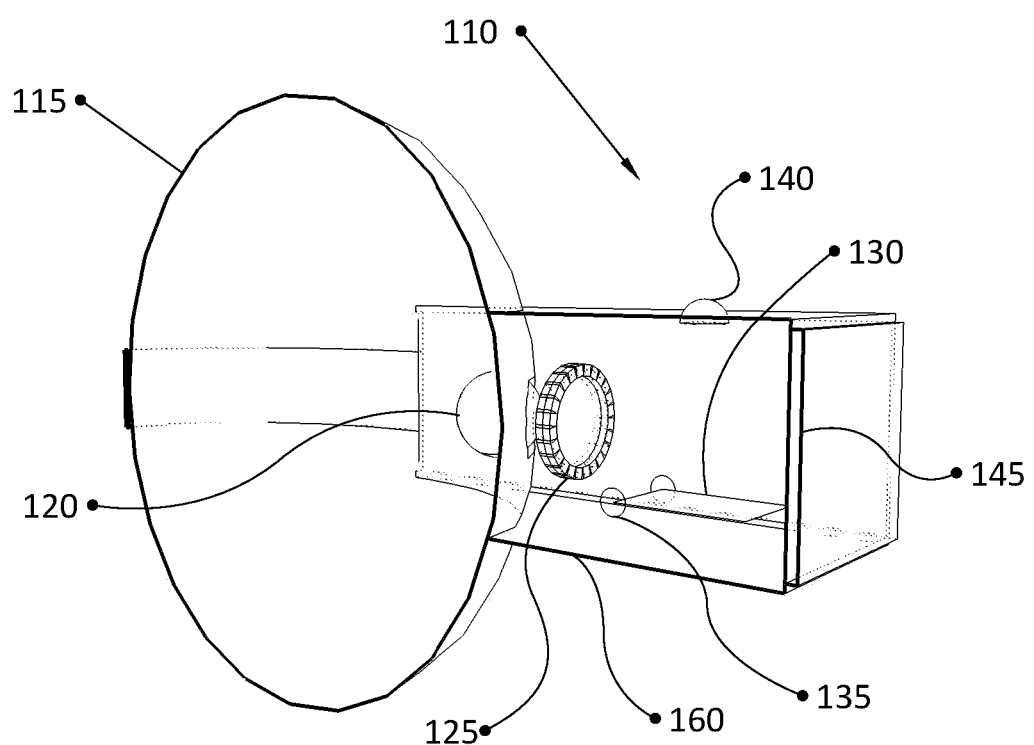
FIG. 2 is a diagram illustrating a section view of the VR device and person of FIG. 2, according to some embodiments.

FIG. 2 is a diagram illustrating a section view of VR device 110 and head 115 of FIG. 2, according to some embodiments. In FIG. 2, eye 120 is illustrated inside head 115, generally in the location where an eye would be located (the illustrations are approximate), with other components of head 115 being simplified or not shown for the sake of clarity.

Also illustrated in FIG. 2 is adjustable lens 125. Adjustable lens 125 embodiments are further illustrated and discussed in relation to FIG. 4. In general terms, adjustable lens 125 comprises a flexible lens surrounded by an actuator; the actuator may change shape. A change in shape of the actuator may change the shape of flexible lens, thereby changing an optical power of flexible lens.

Also illustrated in FIG. 2 is focus sensor 140. As described further herein, focus sensor 140 may be used to determine a diopter of eye 120 and/or to determine a distance between eye 120 and display 145. Focus sensor 140 is illustrated in FIG. 1 as extending above VR device frame 160. This is for the sake of simplicity and clarity in the illustration; focus sensor 140 may be embedded within VR device frame 160. Focus sensor 140 is also illustrated as being on the top of VR device frame 160. Focus sensor 140 may be located on a side, bottom, or back of VR device frame 160, such as in display 901 (illustrated in FIG. 9). Embodiments of focus sensor 140 are illustrated and discussed further in relation to FIGS. 5A and 5B and FIG. 9.

Also illustrated in FIG. 2 are mirror 130 and mirror actuator 135. As discussed herein, mirror 130 may be deployed in a path between eye 120 and focus sensor 140, such that electromagnetic radiation produced by focus sensor 140 may be directed into eye 120 and such that focus sensor 140 may sense a reflection therefrom. As illustrated further in FIGS. 3A-3D, mirror 130 is illustrated as being capable of moving into the path between eye 120 and focus sensor 140; in embodiments, mirror 130 may maintain a fixed location in the path and a refractive index of mirror 130 may be adjustable, such as through, for example, liquid crystals within mirror 130. By altering the refractive index of mirror 130, it may be switched between being substantially transparent to electromagnetic radiation from display 145 and/or focus sensor 140, to reflecting electromagnetic between focus sensor 140 and eye 120. Mirror actuator 135 may be an electric stepper motor, a limited angle torque motor, a linear actuator or the like.

Also illustrated in FIG. 2 is display 145 (which may also be referred to herein as "display monitor"). Display 145 may comprise one or more substantially flat panel video displays. Display 145 may emit images seen by eye 120. Not illustrated in FIG. 2 are audio output components, such as speakers, headphones, earbuds, or the like, which may output audio.

Also illustrated in FIG. 2 is VR device frame 160. VR device frame 160 is an example of any structure capable of holding display 145, focus sensor 140, and adjustable lens 125 in a fixed relationship with eye 120, generally in relationship to head 115.

Figure 3A:
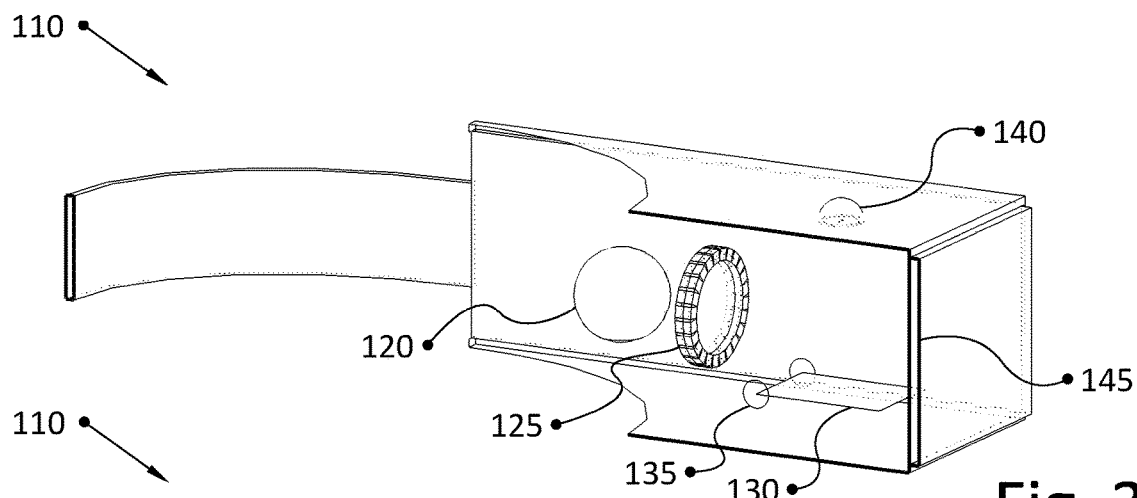
FIG. 3A is a diagram illustrating a section view of the VR device of FIG. 1, an eye of a person, with a sensor mirror not deployed, according to some embodiments.
Figure 3B:
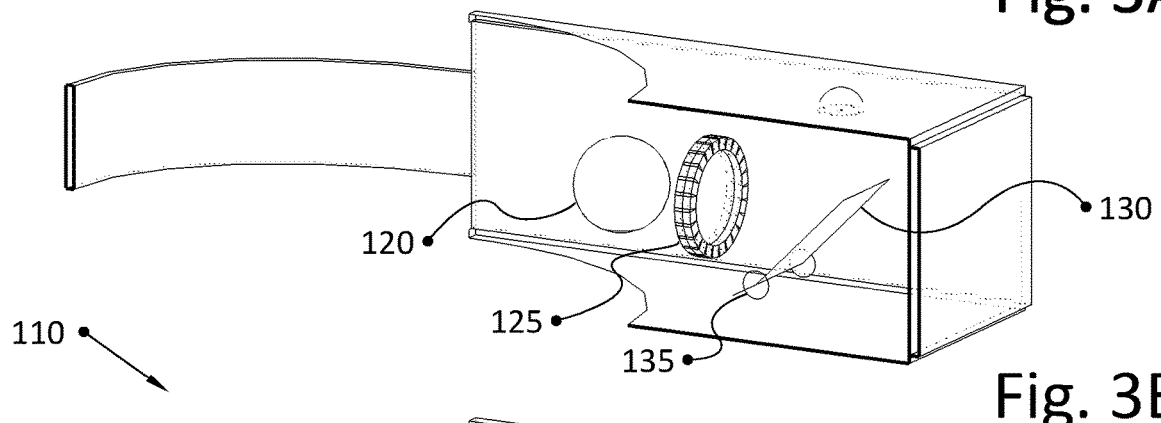
FIG. 3B is a diagram illustrating a section view of the VR device of FIG. 1, an eye of a person, and with a sensor mirror deployed, according to some embodiments.
Figure 3C:
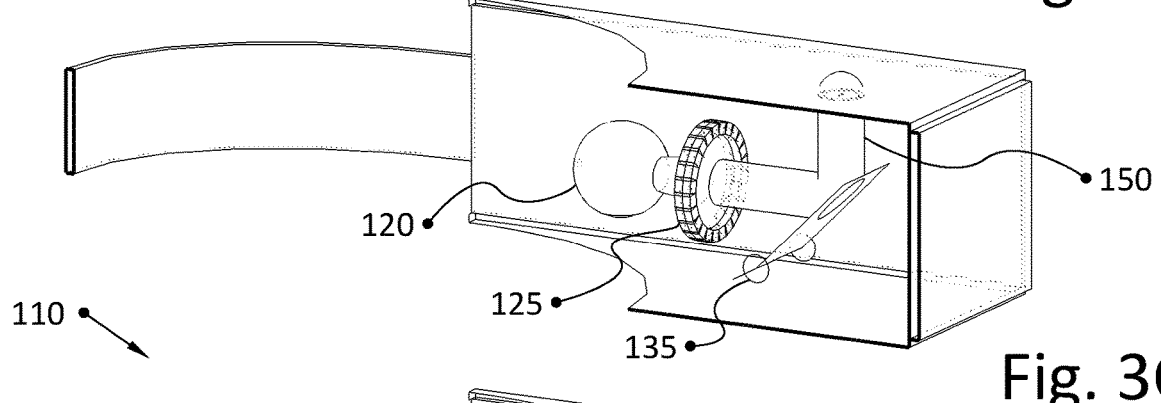
FIG. 3C is a diagram illustrating a section view of the VR device of FIG. 1, an eye of a person, with a sensor mirror deployed, with electromagnetic radiation being emitted by a sensor, being reflected by the mirror, and focused into the eye by an adjustable lens, according to some embodiments.
Figure 3D:
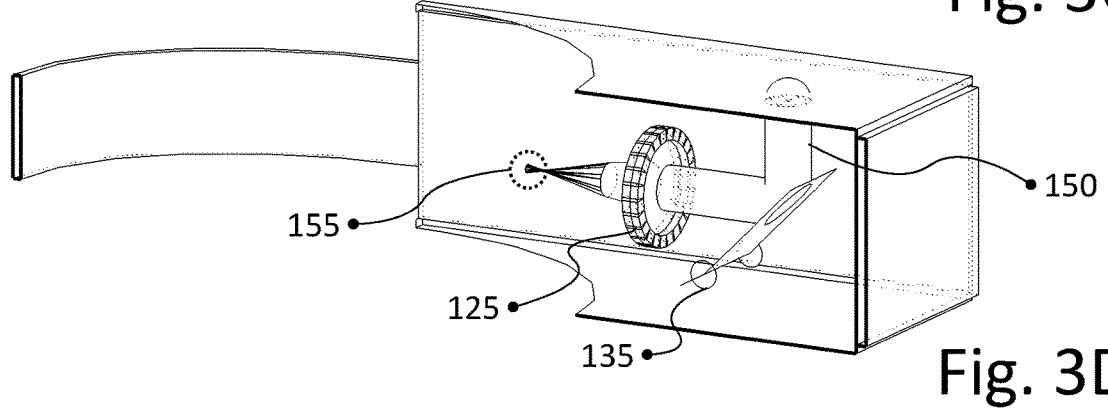
FIG. 3D is a diagram illustrating a section view of the VR device of FIG. 1, with a sensor mirror deployed, with electromagnetic radiation being emitted by a sensor, and illustrating focus of the electromagnetic radiation onto an area equivalent to a retina of an eye, according to some embodiments.

FIG. 3A is a diagram illustrating a section view of VR device 110 of FIG. 1, eye 120 of a person, focus sensor 140, mirror actuator 135, mirror 130, with mirror 130 not deployed, according to some embodiments. FIG. 3B is a diagram illustrating a section view of VR device 110 of FIG. 1, with mirror 130 deployed, according to some embodiments. FIG. 3C is a diagram illustrating a section view of VR device 110 of FIG. 1 with mirror 130 deployed, with electromagnetic radiation 150 being emitted by focus sensor 140, reflected by mirror 130, focused by adjustable lens 125, and passing onto and into eye 120, according to some embodiments. FIG. 3D is a diagram illustrating a section view of VR device 110 of FIG. 1 with mirror 130 deployed, with electromagnetic radiation 150 being emitted by focus sensor 140, reflected by mirror 130, focused by adjustable lens 125, and passing onto and into eye 120, but with eye 120 not shown, to illustrate retina 155 within eye 120, onto which electromagnetic radiation 150 emitted by focus sensor 140 falls, according to some embodiments.

A portion of electromagnetic radiation 150 emitted by focus sensor 140 reflects off of retina 155 and/or off of eye 120 and may be detected by electromagnetic radiation receivers in focus sensor 140. By measuring time-of-flight of the electromagnetic radiation, a distance between focus sensor 140 and eye 120 and/or retina 155 may be determined. The distance between focus sensor 140 and eye 120 and/or retina 155 may be used to adjust a focal power of adjustable lens 125. By emitting coded pulses of electromagnetic radiation from a structure in a focus sensor 140 with a known geometric shape, and by measuring a difference in the time-of-flight for more than one coded pulse of electromagnetic radiation, a determination can be made regarding whether the image on retina 155 is in focus and an estimate of a diopter correction can be made, relative to eye 120 and its ability to focus the electromagnetic radiation. A focal power of adjustable lens 125 can be changed, such as by activating piezoelectric or other actuators around a perimeter of a flexible lens. In an alternative embodiment, a user can provide a diopter of correction, such as a diopter of a lens used by the user and the system can change the focal power of adjustable lens 125. The user may be able to provide feedback to change the focal power of adjustable lens 125.

Figure 4:
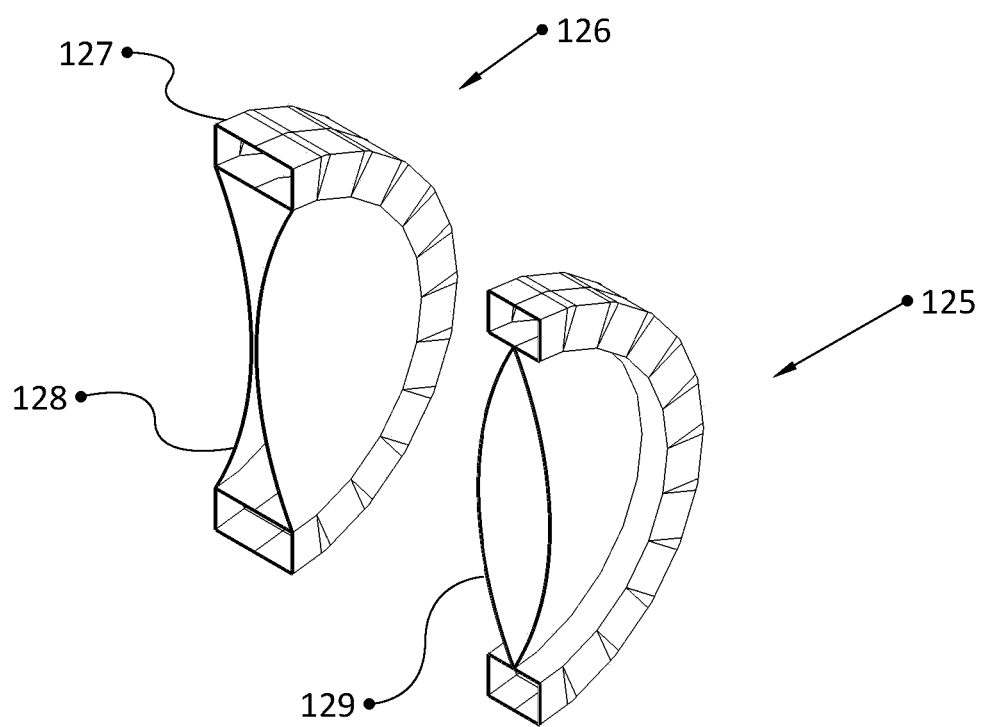
FIG. 4 is a diagram illustrating a section isometric view of two adjustable lenses side-by-side for the sake of comparison, according to some embodiments.

FIG. 4 is a diagram illustrating a section isometric view of two adjustable lenses side-by-side for the sake of comparison, according to some embodiments. Adjustable lens 125 illustrates a convex flexible lens 129; adjustable lens 127 illustrates concave flexible lens 128. When relaxed, the flexible lens may be flat on both sides and may have or provide a zero diopter correction. The adjustable lens may comprise actuators, such as piezoelectric actuators, surrounding the flexible lens, such as in contact with a perimeter of flexible lens, to change the curvature of flexible lens by compressing or expanding its perimeter. Other actuators may be used, such as stepper motors, gas or fluid based actuators, a pair of counter-rotating or the like. Flexible lens may comprise a valve for a fluid which can be pumped into or out of flexible lens to change the curvature of flexible lens and its diopter. By way of example in FIG. 4, piezoelectric actuators 127 are illustrated around perimeter of flexible lens 128. Piezoelectric actuators 127 may be held in a rigid frame which allows piezoelectric actuators 127 to move relative to one another and to compress or expand a perimeter of a flexible lens.

Figure 5A:
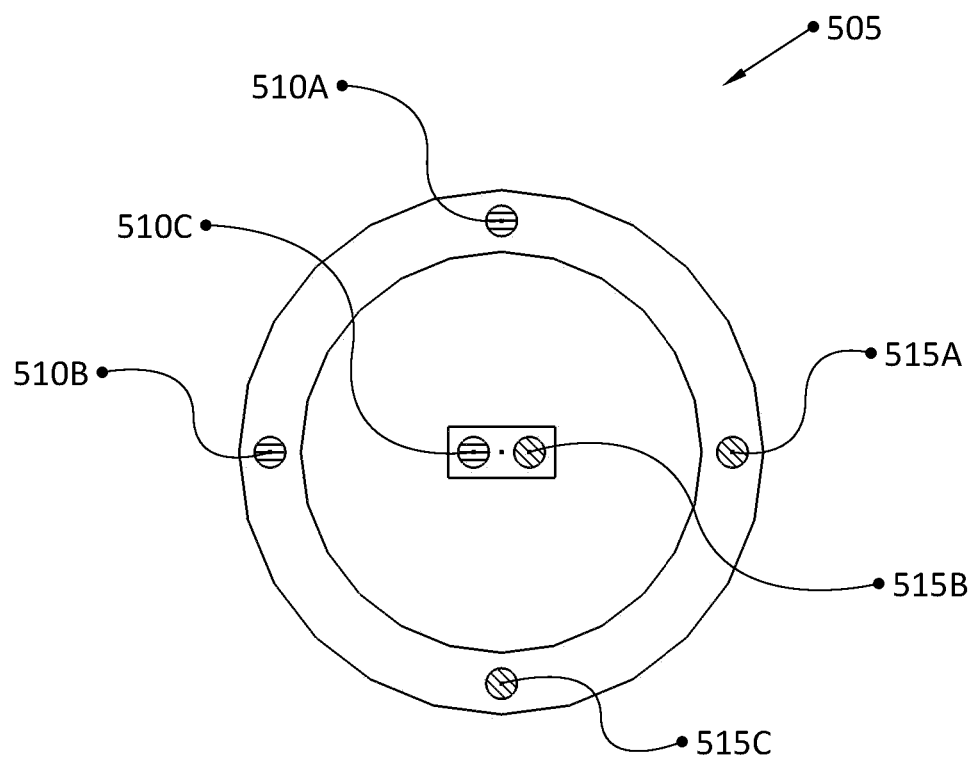
FIG. 5A is a bottom plan view of an electromagnetic transceiver structure of a focus sensor, according to some embodiments.
Figure 5B:
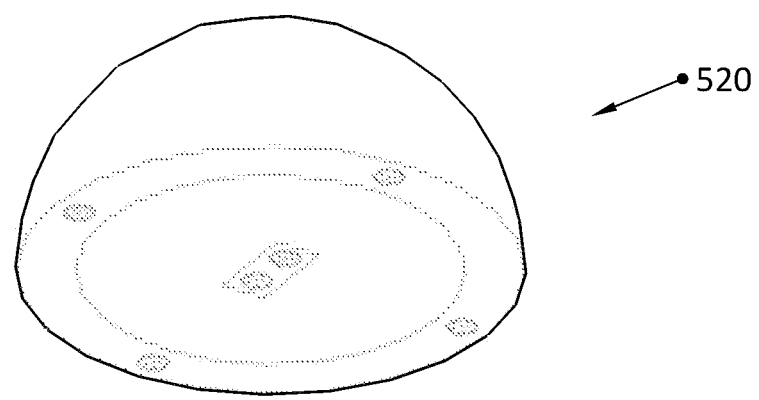
FIG. 5B is a partially transparent, top isometric view of the electromagnetic transceiver structure of a focus sensor, according to some embodiments.

FIG. 5A is a bottom plan view of an electromagnetic transceiver structure of focus sensor 505, according to some embodiments. FIG. 5B is a partially transparent, top isometric view of the electromagnetic transceiver structure focus sensor 505, according to some embodiments. Focus sensor 505 may be similar to focus sensor 140 illustrated in FIG. 2 and FIGS. 3A-3D. Focus sensor 505 may comprise one or more electromagnetic radiation emitters, such as electromagnetic radiation emitters 510A, 510B, and 510C. Electromagnetic radiation emitters 510A, 510B, and 510C may be, for example, light emitting diodes or the like. The electromagnetic radiation emitters may emit in the millimeter (extreme high frequency radio) band, in the infrared band, or in the visible band. Electromagnetic radiation emitters 510A, 510B, and 510C may be accompanied by electromagnetic radiation receivers, such as electromagnetic radiation receivers 515A, 515B, and 515C. The electromagnetic radiation receivers may be sensitive to the spectrum of electromagnetic radiation emitted by the electromagnetic radiation emitters.

The electromagnetic radiation emitters and receivers may be arranged in a geometric shape. For example, in FIGS. 5A and 5B, electromagnetic radiation emitters 510A, 510B, and 510C may be arranged in a first triangular shape while electromagnetic radiation receivers 515A, 515B, and 515C may be arranged in second triangular shape. The first and second triangular shapes may be similar geometric shapes. When used herein, "geometrically similar" shapes are the same shape, though may be of different sizes. For example, two geometrically similar shapes can be obtained, one from another, by uniform scaling, possibly with translation, rotation, and reflection. In the example illustrated in FIG. 5A, the first and second triangular shapes of the emitters and receivers are both right, isosceles triangles, generally arranged in an approximate mirror-image configuration. In alternative embodiments the emitters and receivers may be arranged in one or more lines across display 901 (in which case mirror 130 may not be necessary), an example of which is illustrated further in FIG. 9.

One or more focus sensors may be included in a VR device. As illustrated in FIG. 1, FIG. 2, and FIG. 3 (the latter being section views of one half of a generally symmetrical VR device), two focus sensors may be included in a VR device.

By arranging the emitters and receivers in a known geometric shape, it may be possible to measure a time-of-flight between the emitters and the receivers. Measuring the time-of-flight may be relative to an eye and/or relative to a retina of an eye. Measuring the time-of-flight provides a measurement of the distance traveled by the electromagnetic radiation between the emitters and the receivers, such as with respect to an eye and/or a retina onto which the electromagnetic radiation is falling. If the distance from the emitters/receivers to the display is known, the distance traveled by the electromagnetic radiation between the emitters and the receivers can be used to determine the distance between the eye and/or retina and the display. By encoding information into emitted electromagnetic radiation ("coded signals"), it is possible to distinguish different pulses of electromagnetic radiation. By measuring the time-of-flight of different coded signals emitted and received at different locations on focus sensor, it is possible to determine a structure of a reflection of the electromagnetic radiation, such as, for example, whether the reflection is tightly spaced or spread out. Measurement of time-of-flight of electromagnetic radiation is discussed further in relation to focus sensor logic 800 (illustrated further in FIG. 8).

Figure 6:
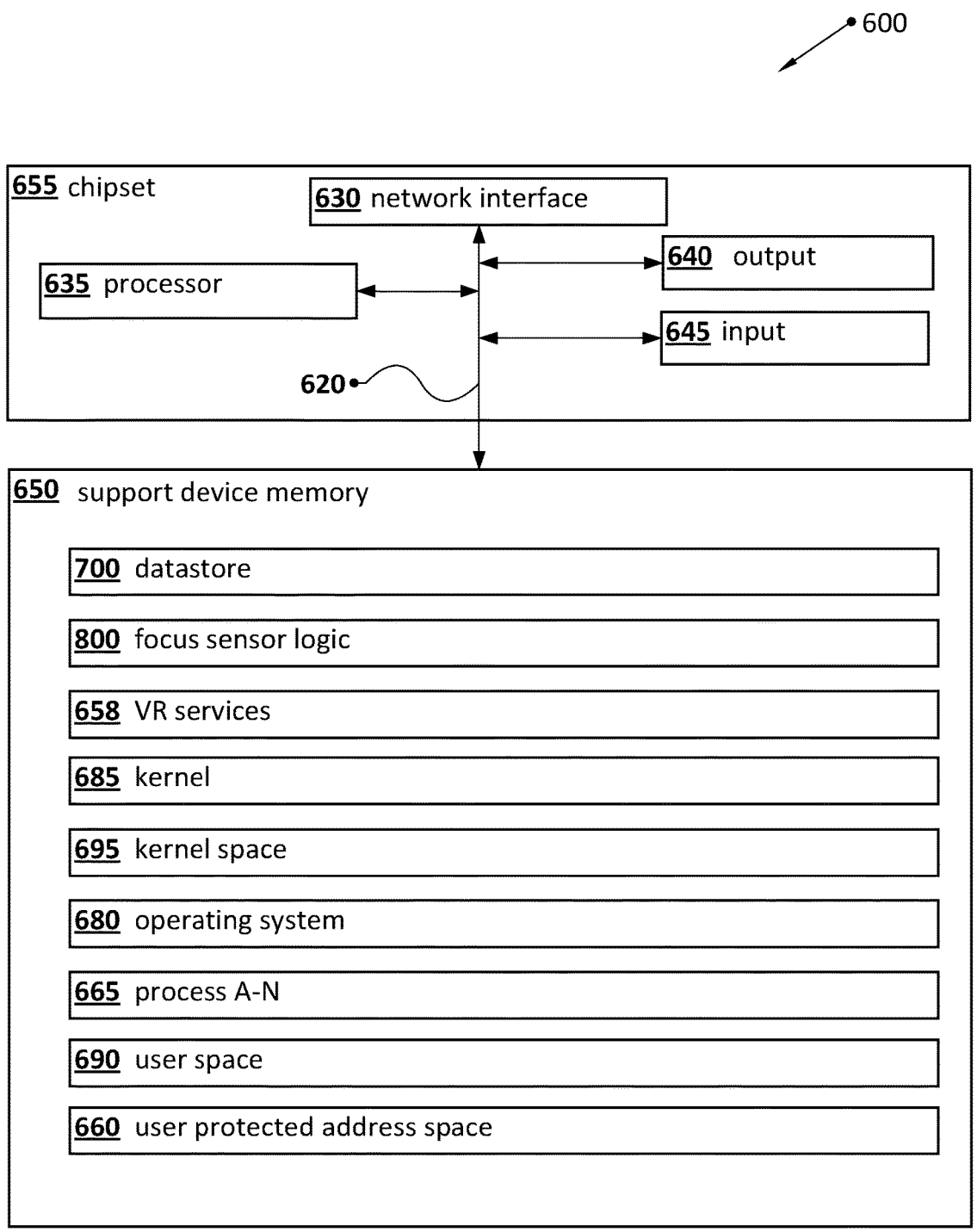
FIG. 6 is a functional block diagram illustrating an example of a VR device for practicing the present disclosure, according to some embodiments.

FIG. 6 is a functional block diagram illustrating an example of support computer 600 for practicing aspects of the present disclosure, according to some embodiments. As discussed above, support computer 600 may be part of a VR device, such as VR device 110; in embodiments, support computer 600 may be a separate component, relative to a VR device, and/or components or parts of support computer 600 may be part of a VR device. Support computer 600 may provide computational and memory services to VR device, such as, for example, network services, codec and other video and audio processing services, VR services (such as OpenGL, user-space device drivers, gesture recognition, voice recognition, compass, inertial measurement unit processing, external image processing, processing of a VR video-audio file, and the like) display driver services, and the like, in addition to focus sensor logic, such as focus sensor logic 800, to operate one or more focus sensor(s) in VR device, as described further herein in relation to FIG. 8.

Support computer 600, except for the teachings of the present disclosure, may include, but is not limited to, a virtual reality or augmented reality display or supporting computers therefore, a server, a workstation computer, a desktop computer, a laptop computer, a tablet computer (e.g., iPad®, GalaxyTab® and the like), an ultraportable computer, an ultramobile computer, a netbook computer and/or a subnotebook computer; a mobile telephone including, but not limited to a smart phone, (e.g., iPhone®, Android®-based phone, Blackberry®, Symbian®-based phone, Palm®-based phone, etc.) and the like. For example, support computer 600 may support and/or be part of a Oculus Rift®, PlayStation VR® and the like.

Support computer 600 may include chipset 655, comprising processor 635, input/output (I/O) port(s) and peripheral device interfaces, such as output interface 640 and input interface 645, and network interface 630, and support device memory 650, all interconnected via bus 620. Network Interface 630 may be utilized to couple processor 635 to a network interface card (NIC) to form connections with network 101, with datastore 700, or to form device-to-device connections with other computers.

Chipset 655 may include communication components and/or paths, e.g., buses 620, that couple processor 635 to peripheral devices, such as, for example, output interface 640 and input interface 645, which may be connected via I/O ports. For example, chipset 655 may include a peripheral controller hub (PCH) (not shown). In another example, chipset 655 may include a sensors hub. Input interface 645 and output interface 640 may couple processor 635 to input and/or output devices that include, for example, user and machine interface device(s) including a display (such as, for example, display 145), a touch-screen display, an adjustable lens (such as, for example, adjustable lens 125), printer, keypad, keyboard, etc., sensor(s) including, for example, focus sensors (such as focus sensor 505), inertial measurement unit(s), camera(s), global positioning system (GPS), etc., storage device(s) including hard disk drives, solid-state drives, removable storage media, etc. I/O ports for input interface 645 and output interface 640 may be configured to transmit and/or receive commands and/or data according to one or more communications protocols. For example, one or more of the I/O ports may comply and/or be compatible with a universal serial bus (USB) protocol, peripheral component interconnect (PCI) protocol (e.g., PCI express (PCIe)), or the like.

Processor 635 may include one or more execution core(s), which may be central processing units ("CPUs") and/or graphics processing units ("GPUs") one or more registers, and one or more cache memor(ies). Processor 635 may include a memory management unit (MMU) to manage memory accesses between processor 635 and support device memory 650. In some embodiments, processor 635 may be configured as one or more socket(s); each socket may include one or more core(s), a plurality of registers and one or more cache memor(ies). Each core may be configured to execute one or more process(es) 665 and/or one or more thread(s). A plurality of registers may include a plurality of general purpose registers, a status register and an instruction pointer. Cache(s) may include one or more cache memories, which may be used to cache focus sensor logic 800 of the present disclosure.

Support device memory 650 may generally comprise a random access memory ("RAM"), a read only memory ("ROM"), and a permanent mass storage device, such as a disk drive or SDRAM (synchronous dynamic random-access memory). Support device memory 650 may store program code for software modules, routines, or logic, such as, for example, focus sensor logic 800 (illustrated and discussed further in relation to FIG. 8) and VR services 658.

Support device memory 650 may also store operating system 680. These software components may be loaded from a non-transient computer readable storage medium 696 into support device memory 650 using a drive mechanism associated with a non-transient computer readable storage medium 696, such as a floppy disc, tape, DVD/CD-ROM drive, memory card, or other like storage medium. In some embodiments, software components may also or instead be loaded via a mechanism other than a drive mechanism and computer readable storage medium 696 (e.g., via network interface 630).

Figure 7:
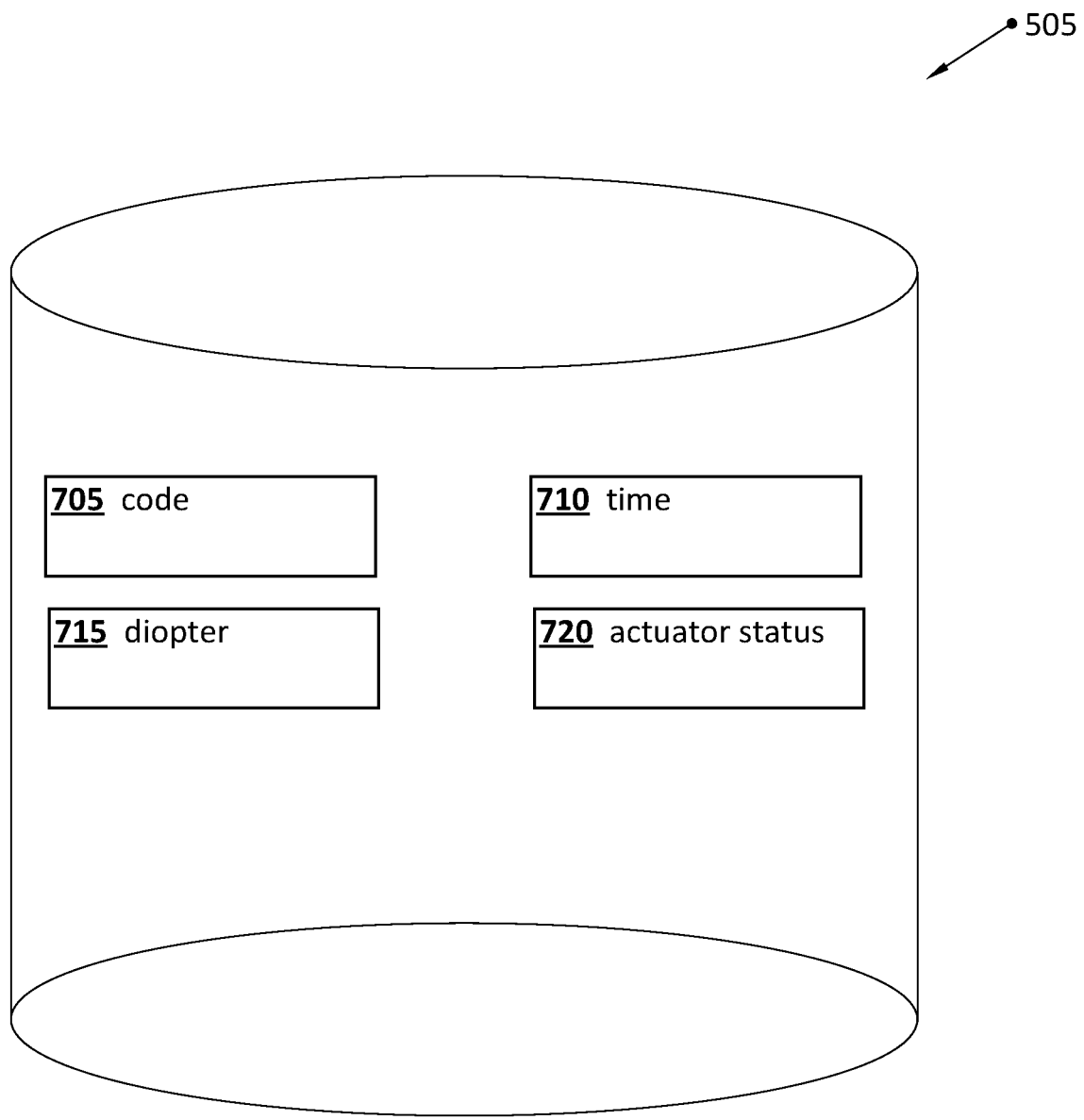
FIG. 7 is a functional block diagram illustrating an example of a datastore which may be used by a VR device for practicing the present disclosure, according to some embodiments.

Support device memory 650 is also illustrated as comprising kernel 685, kernel space 695, user space 690, user protected address space 660, and datastore 700 (illustrated and discussed further in relation to FIG. 7).

Support device memory 650 may store one or more process 665 (i.e., executing software application(s)). Process 665 may be stored in user space 690. Process 665 may include one or more other process 665A . . . 265N, such as corresponding to an executing software application. One or more process 665 may execute generally in parallel, i.e., as a plurality of processes and/or a plurality of threads.

Support device memory 650 is further illustrated as storing operating system 680 and/or kernel 685. The operating system 680 and/or kernel 685 may be stored in kernel space 695. In some embodiments, operating system 680 may include kernel 685. One or more process 665 may be unable to directly access kernel space 695. In other words, operating system 680 and/or kernel 685 may attempt to protect kernel space 695 and prevent access by one or more process 665A . . . 265N.

Kernel 685 may be configured to provide an interface between user processes and circuitry associated with support computer 600. In other words, kernel 685 may be configured to manage access to processor 635, chipset 655, I/O ports and peripheral devices by process 665. Kernel 685 may include one or more drivers configured to manage and/or communicate with elements of support computer 600 (i.e., processor 635, chipset 655, I/O ports and peripheral devices).

Support computer 600 may also comprise or communicate via bus 620 and/or network interface 630 with datastore 700, illustrated and discussed further in relation to FIG. 7. In various embodiments, bus 620 may comprise a high speed serial bus, and network interface 630 may be coupled to a storage area network ("SAN"), a high speed wired or wireless network, and/or via other suitable communication technology. Support computer 600 may, in some embodiments, include many more components than as illustrated. However, it is not necessary that all components be shown in order to disclose an illustrative embodiment.

FIG. 7 is a functional block diagram illustrating an example of a datastore which may be used by a datastore 700 for practicing aspects of the present disclosure, according to some embodiments. Datastore 700 generally should be understood as a datastore used by support computer 600. Datastore 700 may be physically co-located with support computer 600 and/or may be remote therefrom. Datastore 700 may comprise multiple datastores, in and/or remote with respect to support computer 600. Datastore 700 may be distributed.

The components of datastore 700 may include data groups used by modules and/or routines, e.g, code 705, time 710, diopter 715, and actuator status 720 (to be described more fully below). The data groups used by modules or routines illustrated in FIG. 7 may be represented by a cell in a column or a value separated from other values in a defined structure in a digital document or file. Though referred to herein as individual records or entries, the records may comprise more than one database entry. The database entries may be, represent, or encode numbers, numerical operators, binary values, logical values, text, string operators, references to other database entries, joins, conditional logic, tests, and similar.

The components of datastore 700 are discussed further herein in the discussion of other of the Figures. In overview, code 705 records may record codes assigned to an electromagnetic emission by focus sensor logic 800. One or more code 705 vales or identifiers thereof may be encoded into different electromagnetic emissions by focus sensor. In overview, time 710 records may record time values, such as the time of transmission or reception of an electromagnetic emission. In overview, diopter 715 records may record a diopter of an eye, of a visual system, of a lens in a visual system, and the like. Diopter 715 records may record a focal power. Diopter 715 records may record information provided by a user or measured in relation to a user. In overview, actuator status 720 records may record a status of an actuator used to control a flexible lens, whether of a piezoelectric actuator, a fluid pump, or the like.

Figure 8:
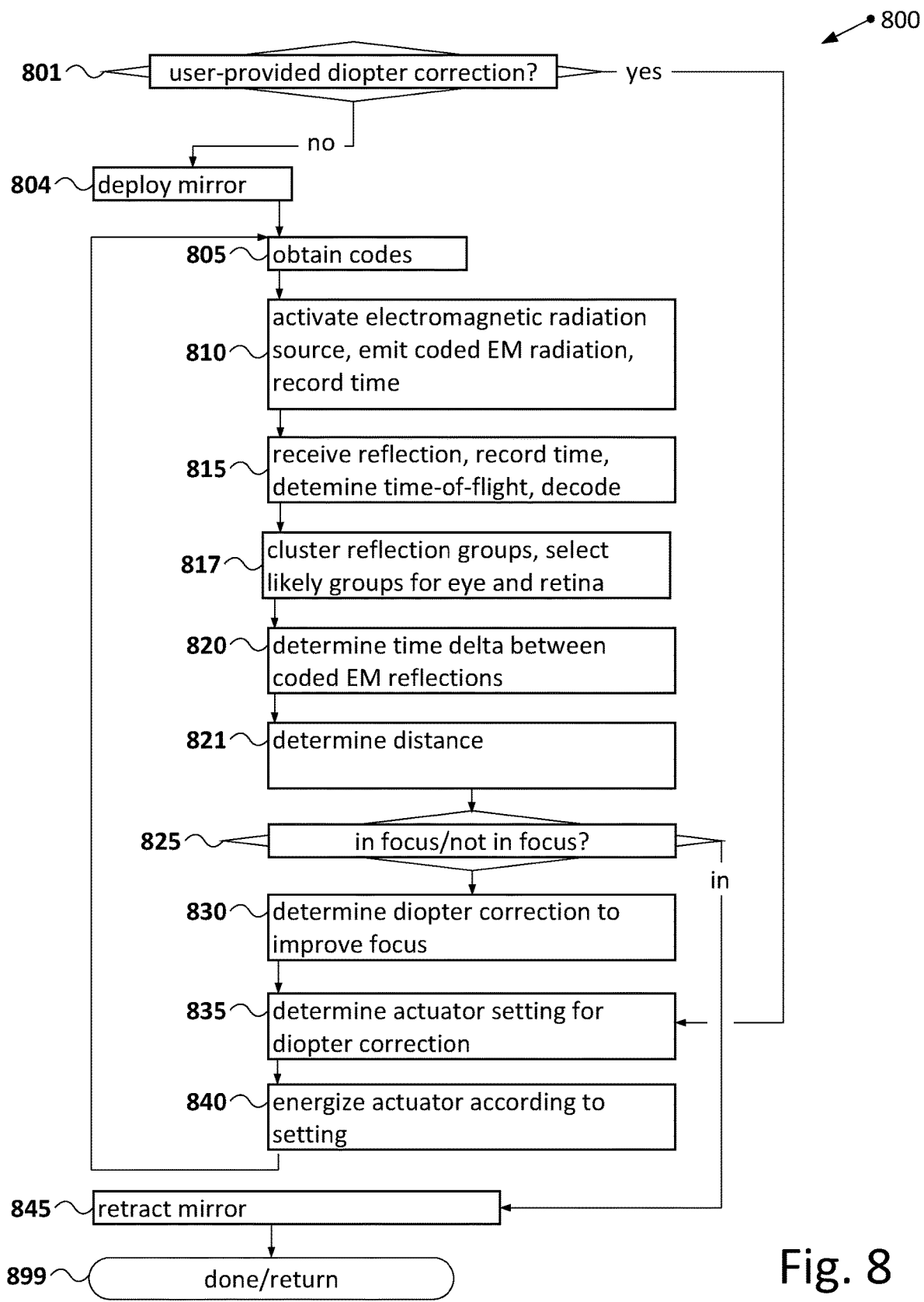
FIG. 8 is a flow diagram illustrating an example of a method performed by focus sensor logic of a VR device, according to some embodiments.

FIG. 8 is a flow diagram illustrating an example of a method performed by focus sensor logic 800 by a VR device, such as VR device 110, and/or by a support computer for a VR device, such as support computer 600, according to some embodiments.

Figure 9:
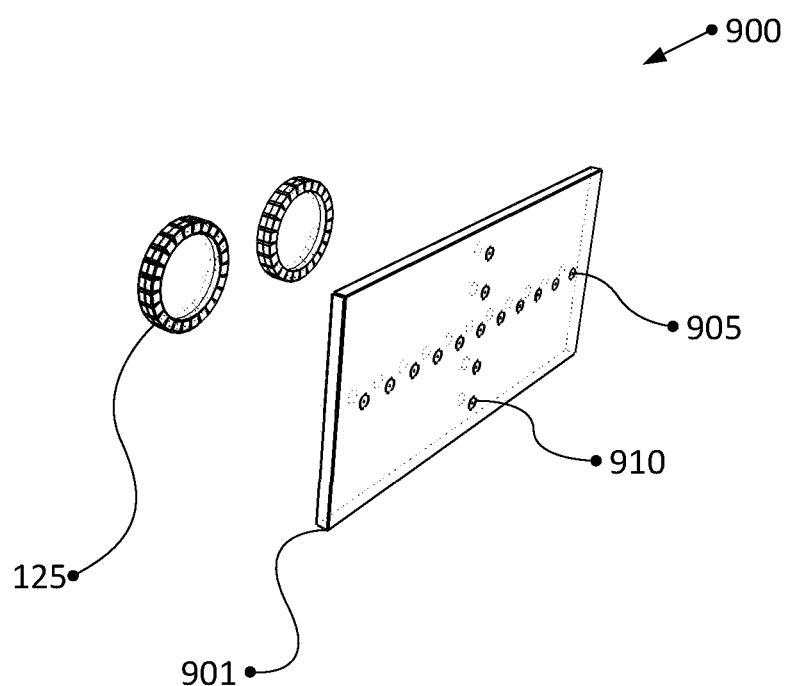
FIG. 9 is a diagram illustrating an isometric view of a display incorporating a distance sensor and an adjustable lens, according to some embodiments.

At decision block 801, focus sensor logic 800 may determine whether a user-provided diopter correction setting is available or received, such as from user input. If negative or equivalent at decision block 801, at block 804, focus sensor logic 800 may deploy a sensor mirror to reflect electromagnetic radiation from a distance sensor into an eye (or eyes) of a user of a VR device. Examples of such a mirror are illustrated in FIG. 3A-3D, at mirror 130. Deployment of a mirror may be optional, for example, in cases in which distance sensor is not incorporated into a display of the VR device (as illustrated in FIG. 9), but is located on a top, bottom, or side of VR device.

At block 805, focus sensor logic 800 may obtain or derive codes to be encoded into electromagnetic radiation transmitted toward a user. The code(s) may be stored as, for example, one or more code 705 records.

At block 810, focus sensor logic 800 may activate an electromagnetic radiation source, such as a transmitter in distance sensor, such as electromagnetic radiation emitter 510A. More than one transmitter may be activated at a time and/or a set of electromagnetic radiation emitters may be activated in rapid succession. At block 810, focus sensor logic 800 may emit electromagnetic radiation from activated transmitter(s); the emitted electromagnetic radiation may be encoded with the code(s) of block 805. At block 810, focus sensor logic 800 may record the time when the electromagnetic radiation was emitted. The time may be recorded as one or more time 710 records. The time may record a range of time across which one or more pulses of electromagnetic radiation are transmitted.

At block 815, focus sensor logic 800 may receive one or more reflections of the electromagnetic radiation transmitted in block 810. The reflections may comprise multiple reflections, such as off of adjustable lens, off of an exterior of eye, and off of a retina. At block 815, the time of receipt of electromagnetic radiation may be recorded, such as in one or more time 710 records. One or more code(s) encoded into the electromagnetic radiation may be decoded. Time-of-flight for the electromagnetic radiation may be determined, such as according to a difference in the time of transmission of the electromagnetic radiation at block 810 and a time of receipt of the electromagnetic radiation at block 815. A power of the received electromagnetic radiation may also be determined.

At block 817, focus sensor logic 800 may cluster groups of electromagnetic radiation reflections, if any, according to time of receipt. Focus sensor logic 800 may select from the groups those clusters consistent with reflections from an eye and/or from a retina. For example, reflections may return from an adjustable lens, slightly in advance of reflections from an eye. For example, background electromagnetic radiation may be detected, but without coding and/or below a threshold. These reflections may be removed from analysis.

At block 820, focus sensor logic 800 may determine a time difference between transmission and reception for electromagnetic radiation, individually and/or as may have been grouped in clusters. The time difference may be determined with respect to different transmitters and different receivers in a structured light sensor. For example, if a coded signal is transmitted by a particular transmitter in a structured light sensor, it may be possible to detect differences in time-of-flight for the coded signal with respect to different receivers in a structured light sensor, because there are different distances between the transmitter and the different receivers in the structured light sensor.

At block 821, focus sensor logic 800 may determine a distance traveled by the electromagnetic radiation in the cluster(s), as it traveled from the focus sensor, to the reflective surface, and back to the focus sensor. With a known and fixed distance between the focus sensor and a display in the VR device, wherein the fixed distance is defined by the structure of the VR device, it may be possible to determine the distance between the display and the source of reflection. By selecting sources of reflection which are likely to be an eye and/or a retina, it is possible to change a focal power of an adjustable lens, based on the distance between the display (or the focus sensor) and the source of reflection.

At decision block 825, focus sensor logic 800 may determine whether the time difference for different transmission/reception events at the different receivers in the structured light sensor, relative to reflection clusters identified as probably originating from a retina, is characteristic of being in focus or not in focus. For example, when the eye is able to focus incoming light, the time-of-flight for a coded signal to from a transmitter to different receivers in a structured light sensor may be spread out in a characteristic pattern, such as a tight pattern. In contrast, when the eye is not able to focus incoming light, the time-of-flight for the coded signal relative to the different receivers in the structured light sensor may be spread out in a different characteristic pattern, such as a broader pattern.

At block 830, if not in focus at decision block 825, focus sensor logic 800 may determine a diopter correction to improve focus. The diopter correction may be approximate. The diopter correction may be a direction of correction, such as a negative or positive correction. A negative or positive correction may indicate a degree of correction, such as one or more increments, such as a fifth, tenth, or quarter of a diopter.

At block 835, which may follow block 830 or decision block 801, focus sensor logic 800 may determine an actuator setting to achieve the diopter correction of block 830 or the user provided diopter correction, such as a voltage to apply to a piezoelectric actuator, an amount of fluid to pump into a flexible lens, and the like. The actuator setting may be based, at least in part, on a previous status of the actuator, as may have been recorded in an actuator status 720 record.

At block 840, focus sensor logic 800 may energize the actuator according to the actuator setting of block 835. Either the actuator setting of block 835 and/or feedback from the actuator, such as after energizing, may be stored as, for example, one or more actuator status 720 records.

Following block 840, focus sensor logic 800 may return to block 805 to continue to iterate until decision block 825 determines that focus has been achieved, or until a number of iterations have been performed, or until an interrupt event occurs, such as a user input.

At block 845, which may follow decision block 825 if found to be in focus or equivalent, or upon a number of iterations, or an interrupt event, focus sensor logic 800 may retract sensor mirror 804.

At done block 899, focus sensor logic 800 may conclude and/or return to a process which may have called it.

FIG. 9 is a diagram illustrating an isometric view of a display 901 incorporating a distance sensor and an adjustable lens, according to some embodiments. As illustrated in FIG. 9, display 901 may include one or more transmitter 905 and receiver 910. The size of transmitter 905 and receiver 910 are exaggerated in FIG. 9; actual implementations may be much smaller. Transmitter 905 and receiver 910 are similar to those illustrated and discussed in relation to FIGS. 5A and 5B and may be considered structured light or structured electromagnetic radiation sensors, except that they may be located in display 905. One or more transmitter 905 elements may be located in both horizontal and vertical sites in display 901. Similarly, one or more receiver 910 elements may be located in both horizontal and vertical sites in display 901. With transmitter 905 and receiver 910 located in display 901, a moveable mirror may not be necessary, as transmitter 905 and receiver 910 may be able to transmit directly into the user's eyes, without deploying a mirror.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions. USB (Universal serial bus) may comply or be compatible with Universal Serial Bus Specification, Revision 2.0, published by the Universal Serial Bus organization, Apr. 27, 2000, and/or later versions of this specification, for example, Universal Serial Bus Specification, Revision 3.1, published Jul. 26, 2013. PCIe may comply or be compatible with PCI Express 3.0 Base specification, Revision 3.0, published by Peripheral Component Interconnect Special Interest Group (PCI-SIG), November 2010, and/or later and/or related versions of this specification.

Following are examples:

Example 1

An apparatus to display images, comprising: a display monitor; an adjustable lens arrangement; a sensor arrangement disposed before an eye of a user of the apparatus, wherein the sensor arrangement is to determine at least one of a distance between the display monitor and the eye of the user of the apparatus or whether the eye of the user of the apparatus is able to focus images from the display monitor; a focus arrangement to adjust an optical power of the adjustable lens arrangement such that an image projected by the display monitor is in focus in the eye or on a retina of the user of the apparatus.

Example 2

The apparatus according to Example 1, wherein the sensor arrangement comprises an infrared proximity sensor and wherein the sensor arrangement is to transmit an infrared electromagnetic radiation from a transmitter onto the eye or retina of the user of the apparatus, wherein the infrared proximity sensor is to sense a reflection of the infrared electromagnetic radiation with a receiver and measure a distance between the transmitter and the eye or retina of the user.

Example 3

The apparatus according to Example 2, wherein the sensor arrangement comprises a moveable mirror, wherein the sensor arrangement is to insert the moveable mirror into a path between the eye of the user and the display monitor, and wherein the sensor arrangement is to transmit the infrared electromagnetic radiation from the transmitter, onto the moveable mirror and onto the eye or a retina of the user of the apparatus, wherein the infrared proximity sensor is to sense the reflection of the infrared electromagnetic radiation with the receiver and measure the distance between the transmitter and the eye or retina of the user.

Example 4

The apparatus according to any one of Example 2 or Example 3, wherein to measure the distance between the transmitter and the eye or retina of the user comprises to measure the distance based on a measured time-of-flight of the infrared electromagnetic radiation.

Example 5

The apparatus according to Example 3, wherein the transmitter comprises three infrared transmitters in a first triangular shape and wherein the receiver comprises three infrared receivers in a second triangular shape, wherein the first and second triangular shapes are geometrically similar shapes and wherein first and second triangular shapes are proximate at an equivalent vertex in each triangular shape and wherein the first and second triangular shapes are arranged relative to one another in a mirror-image pattern.

Example 6

The apparatus according to Example 1, wherein to determine whether the eye of the user of the apparatus is able to focus images from the display monitor, the sensor arrangement is to obtain a diopter correction from a human input or is to determine a diopter correction based on a measurement with a structured electromagnetic radiation sensor.

Example 7

The apparatus according to Example 2, wherein the sensor arrangement comprises a structured electromagnetic radiation sensor, wherein the structured electromagnetic radiation sensor comprises a set of infrared transmitters and a set of infrared receivers, and wherein the electromagnetic radiation comprises coded signals, and wherein the sensor arrangement is to detect the coded signals at the set of infrared receivers, determine a time-of-flight for each of the coded signals, and determine whether the reflection is in focus based on a difference between the time-of-flight for each of the coded signals, and wherein the focus arrangement is to adjust the optical power of the adjustable lens arrangement based on whether the reflection is in focus.

Example 8

The apparatus according to Example 7, wherein the structured electromagnetic radiation sensor is embedded in the display monitor.

Example 9

The apparatus according to any one of Example 1 to Example 8, wherein the focus arrangement comprises a piezoelectric actuator around a flexible lens, wherein the focus arrangement is to activate the piezoelectric actuator to expand or contract an outer perimeter of the flexible lens to adjust the optical power of the adjustable lens.

Example 10

The apparatus according to Example 9, wherein the flexible lens is one of concave or convex.

Example 11

The apparatus according to Example 9, wherein the piezoelectric actuator comprises a set of piezoelectric actuators radially arranged around the flexible lens.

Example 12

The apparatus according to any one of Example 1 to Example 8, wherein the apparatus is a virtual reality display apparatus.

Example 13

The apparatus according to any one of Example 1 to Example 8, wherein the apparatus is to output the image on the display monitor.

Example 14

A computer implemented method of displaying images, comprising: transmitting an infrared electromagnetic radiation onto or into the eye, sensing a reflection of the infrared electromagnetic radiation with a receiver and determining at least one of a distance between a display monitor and the eye or whether the eye is able to focus an image from the display monitor, adjusting an optical power of an adjustable lens based on at least one of the distance or the determination regarding whether the eye is able to focus an image from the display monitor, and displaying an image on the display monitor.

Example 15

The method according to Example 14, wherein determining a distance between the transmitter and the eye comprises determining the distance based on a time-of-flight of the infrared electromagnetic radiation from a transmitter to the eye.

Example 16

The method according to Example 15, wherein the time-of-flight of the infrared electromagnetic radiation from the transmitter to the eye comprises the time-of-flight of the infrared electromagnetic radiation from a transmitter to a retina of the eye.

Example 17

The method according to Example 14, further comprising determining whether the eye is able to focus the image from the display monitor based on at least one of a human input or a measurement with a structured electromagnetic radiation sensor.

Example 18

The method according to Example 15, further comprising transmitting and receiving coded signals through a set of infrared transmitters and a set of infrared receivers, determining the time-of-flight for each coded signal, determining whether the electromagnetic radiation is in focus in the eye based on at least one difference among the time-of-flight for each coded signal, and adjusting the optical power of the adjustable lens based on whether the electromagnetic radiation is in focus.

Example 19

The method according to Example 18, further comprising clustering the coded signals into a set of reception time clusters, selecting a reception time cluster corresponding to the eye, and determining whether the electromagnetic radiation is in focus in the eye with respect to the reception time cluster corresponding to the eye.

Example 20

The method according to Example 15, wherein adjusting the optical power of the adjustable lens comprises energizing a piezoelectric actuator around a flexible lens.

Example 21

The method according to Example 20, wherein energizing the piezoelectric actuator comprises energizing a set of piezoelectric actuators radially arranged around the flexible lens.

Example 22

The method according to Example 14, further comprising inserting a moveable mirror into a path between the eye and the display monitor, transmitting the infrared electromagnetic radiation onto the moveable mirror and into the eye, sensing the reflection of the infrared electromagnetic radiation with the receiver, determining at least one of the distance between the display monitor and the eye or whether the eye is able to focus the image from the display monitor, adjusting an optical power of an adjustable lens based on at least one of the distance or whether the eye is able to focus the image from the display monitor, removing the moveable mirror from the path, and displaying the image on the display monitor.

Example 23

An apparatus to display images, comprising: means to display an image from a monitor into an eye of a user of the apparatus; sensor means disposed between the display monitor and the eye of the user of the apparatus to sense at least one of a distance between the display monitor and the eye or whether the eye is able to focus the image from the display monitor; means to adjust an optical power of an adjustable lens based on at least one of the distance or whether the eye is able to focus the image from the display monitor such that the image is in focus in the eye of the user.

Example 24

The apparatus according to Example 23, wherein the sensor means comprises an infrared proximity sensor.

Example 25

The apparatus according to Example 24, wherein the sensor means further comprise means transmit an electromagnetic radiation from a transmitter onto or into the eye, means to sense a reflection of the electromagnetic radiation with a receiver, and means to measure a distance between the transmitter and the eye based on the reflection.

Example 26

The apparatus according to Example 25, wherein the means to measure the distance between the transmitter and the eye comprises means to measure the distance based on a time-of-flight of the infrared electromagnetic radiation.

Example 27

The apparatus according to Example 26, wherein means to measure the distance based on a time-of-flight of the infrared electromagnetic radiation comprises means to measure the distance based on a time-of-flight of the infrared electromagnetic radiation between the transmitter and a retina of the eye.

Example 28

The apparatus according to Example 25, further comprising means to insert a moveable mirror into a path between the eye and the display monitor and wherein the transmitter comprises three IR transmitters in a first triangular shape and wherein the receiver comprises three IR receivers in a second triangular shape, wherein the first and second triangular shapes are geometrically similar shapes, wherein first and second triangular shapes are proximate at an equivalent vertex in each triangular shape, and wherein the first and second triangular shapes are arranged in a mirror-image pattern.

Example 29

The apparatus according to Example 23, wherein means to determine whether the eye is able to focus the image from the display monitor comprises means to sense the diopter with a structured electromagnetic radiation sensor.

Example 30

The apparatus according to Example 29, wherein the structured electromagnetic radiation sensor further comprises means to transmit coded signals with a set of infrared transmitters, means to detect the coded signals at a set of infrared receivers, means to determine a time-of-flight of the coded signals and means to determine whether the reflection is in focus based on a difference among the time-of-flight of the coded signals, and means to adjust the optical power of the adjustable lens based on whether the reflection is in focus.

Example 31

The apparatus according to Example 30, wherein the structured electromagnetic radiation sensor is embedded in the display monitor.

Example 32

The apparatus according to any one of Example 23 to Example 31 Example 30, wherein the adjustable lens comprises a piezoelectric actuator around a flexible lens, and further comprising means to activate the piezoelectric actuator to expand or contract an outer perimeter of the flexible lens to adjust the optical power of the adjustable lens.

Example 33

The apparatus according to any one of Example 23 to Example 30, wherein the apparatus is a virtual reality display apparatus.

Example 34

The apparatus according to any one of Example 23 to Example 30, further comprising means to output the image on the display monitor.

Example 35

The apparatus according to any one of Example 23 to Example 31, further comprising means to cluster reflections into a set of clusters and means to select a cluster in the set of cluster reflections corresponding to the eye.

Example 36

One or more computer-readable media comprising instructions that cause a computer device, in response to execution of the instructions by a processor of the computer device, to: display images from a monitor into an eye of a user of the computer device; determine at least one of a distance between the display monitor and the eye of the user or whether the eye is able to focus the image from the display monitor with a sensor disposed in front of the eye of the user; adjust an optical power of an adjustable lens based on at least one of the distance or whether the eye is able to focus the image from the display monitor such that the image is in focus in the eye.

Example 37

The computer-readable media according to Example 36, wherein the sensor comprises an infrared proximity sensor.

Example 38

The computer-readable media according to Example 36, wherein the instructions are further to cause the processor to transmit an electromagnetic radiation from a transmitter and into the eye, sense a reflection of the electromagnetic radiation with a receiver, and measure a distance between the transmitter and the eye.

Example 39

The computer-readable media according to Example 38, wherein the instructions are further to cause the processor to measure the distance between the transmitter and the eye according to a time-of-flight of the infrared electromagnetic radiation.

Example 40

The computer-readable media according to Example 39, wherein the instructions are further to cause the processor to measure the distance between the transmitter and the eye according to the time-of-flight of the infrared electromagnetic radiation between the transmitter and the eye.

Example 41

The computer-readable media according to Example 38, wherein the transmitter comprises three IR transmitters in a first triangular shape and wherein the receiver comprises three IR receivers in a second triangular shape, wherein the first and second triangular shapes are geometrically similar shapes, wherein first and second triangular shapes are proximate at an equivalent vertex in each triangular shape, and wherein the first and second triangular shapes are arranged in a mirror-image pattern.

Example 42

The computer-readable media according to Example 36, wherein the sensor comprises a structured electromagnetic radiation sensor and wherein the instructions further cause the processor to transmit coded signals with a set of infrared transmitters, detect the coded signals at a set of infrared receivers, determine a set of time-of-flight values of the coded signals, and determine whether the eye is able to focus the image from the display monitor based on a difference between the set of time-of-flight values, and adjust the optical power of the adjustable lens based on whether the eye is able to focus the image from the display monitor.

Example 43

The computer-readable media according to any one of Example 36 to Example 42, wherein the adjustable lens comprises a piezoelectric actuator around a flexible lens, and wherein the instructions further cause the processor to activate the piezoelectric actuator to expand or contract an outer perimeter of the flexible lens to adjust the optical power of the adjustable lens.

Example 44

The computer-readable media according to any one of Example 36 to Example 42, wherein the computer device is a virtual reality display device.

Example 45

The computer-readable media according to any one of Example 36 to Example 42, wherein the instructions are further to cause the processor to output the image on the display monitor.

Example 46

The computer-readable media according to any one of Example 36 to Example 42, wherein the instructions are further to cause the processor to cluster reflections into a set of clusters and select a cluster in the set of cluster reflections corresponding to the eye.

Example 47

An computer system to adjust an optical power of an adjustable lens, comprising: a computer processor and a memory, a display monitor, a sensor disposed before an eye of a user of the system, and an adjustable lens disposed between the display monitor and the eye of the user; wherein the memory comprises instructions, wherein the instructions, when executed by the computer processor, cause the computer processor to: determine with sensor data from the sensor, at least one of a distance between the display monitor and the eye of the user or whether the eye of the user is able to focus images from the display and adjust an optical power of the adjustable lens based on at least one of the distance or whether the eye of the user is able to focus images from the display such that an image on the display monitor is in focus in the eye of the user.

Example 48

The system according to Example 47, wherein the sensor comprises an infrared proximity sensor and wherein the instructions are further to cause the processor to transmit an electromagnetic radiation from a transmitter onto or into the eye, sense a reflection of the electromagnetic radiation with a receiver, and determine a distance between the transmitter and the eye of the user.

Example 49

The system according to Example 48, wherein the instructions are further to cause the processor to insert a moveable mirror into a path between the eye of the user and the display monitor, to transmit an electromagnetic radiation from a transmitter onto the moveable mirror and into the eye of the user, sense a reflection of the electromagnetic radiation with a receiver, and determine a distance between the transmitter and the eye.

Example 50

The system according to at least one of Example 48 or Example 49, wherein the instructions are further to cause the processor to determine the distance between the transmitter and the eye of the user according to a time-of-flight of the infrared electromagnetic radiation.

Example 51

The system according to Example 49, wherein the transmitter comprises three infrared transmitters in a first triangular shape and wherein the receiver comprises three infrared receivers in a second triangular shape, wherein the first and second triangular shapes are geometrically similar shapes, wherein first and second triangular shapes are proximate at an equivalent vertex in each triangular shape, and wherein the first and second triangular shapes are arranged in a mirror-image pattern.

Example 52

The system according to Example 47, wherein the sensor comprises a structured electromagnetic radiation sensor and wherein the instructions further cause the processor to transmit coded signals with a set of infrared transmitters, detect the coded signals at a set of infrared receivers, determine a set of time-of-flight values of the coded signals, and determine whether the eye is able to focus the images from the display monitor based on a difference among the set of time-of-flight values, and adjust the optical power of the adjustable lens based on whether the eye is able to focus the images from the display monitor.

Example 53

The system according to any one of Example 47 to Example 52, wherein the adjustable lens comprises a piezoelectric actuator around a flexible lens, and wherein the instructions further cause the processor to activate the piezoelectric actuator to expand or contract an outer perimeter of the flexible lens to adjust the optical power of the adjustable lens.

Example 54

The system according to any one of Example 47 to Example 52, wherein the system is a virtual reality display device.

The invention claimed is:
1. A computer implemented method of displaying images, comprising:
    transmitting an electromagnetic radiation onto or into an eye of a user,
    sensing a reflection of the electromagnetic radiation with a receiver and determining at least one of a distance between a display monitor and the eye or whether the eye is able to focus an image from the display monitor,
    adjusting an optical power of an adjustable lens on a line of sight between the display monitor and the eye based on at least one of the distance or the determination regarding whether the eye is able to focus an image from the display monitor, and displaying an image on the display monitor.

2. The method according to claim 1, further comprising determining whether the eye is able to focus the image from the display monitor based on at least one of a human input or a measurement with a structured electromagnetic radiation sensor.

3. The method according to claim 2, further comprising transmitting coded signals from a set of transmitters in the structured electromagnetic radiation sensor, detecting reflections of the coded signals with a set of receivers in the structured electromagnetic radiation sensor, determining the time-of-flight for each coded signal, determining whether the electromagnetic radiation is in focus in the eye based on at least one difference among the time-of-flight for each coded signal, and adjusting the optical power of the adjustable lens based on whether the electromagnetic radiation is in focus.

4. The method according to claim 3, further comprising clustering the reflections of the coded signals into a set of reception time clusters, selecting a reception time cluster corresponding to the eye, and determining whether the electromagnetic radiation is in focus in the eye with respect to the reception time cluster corresponding to the eye.

5. The method according to claim 1, wherein adjusting the optical power of the adjustable lens comprises energizing a piezoelectric actuator around a flexible lens.

6. The method according to claim 1, further comprising inserting a moveable mirror into a path between the eye and the display monitor, transmitting the electromagnetic radiation onto the moveable mirror and into the eye, sensing the reflection of the electromagnetic radiation with the receiver, determining at least one of the distance between the display monitor and the eye or whether the eye is able to focus the image from the display monitor, adjusting the optical power of the adjustable lens based on at least one of the distance or whether the eye is able to focus the image from the display monitor, removing the moveable mirror from the path, and displaying the image on the display monitor.

7. One or more computer-readable media comprising instructions that cause a computer device, in response to execution of the instructions by a processor of the computer device, to:

display images from a monitor into an eye of a user of the computer device;

determine at least one of a distance between the display monitor and the eye of the user or whether the eye is able to focus the image from the display monitor with a sensor disposed in front of the eye of the user; and adjust an optical power of an adjustable lens on a line of sight between the monitor and the eye based on at least one of the distance or whether the eye is able to focus the image from the display monitor such that the image is in focus in the eye.

8. The computer-readable media according to claim 7, wherein the sensor comprises a structured electromagnetic radiation sensor and wherein the instructions further cause the processor to transmit coded signals with a set of infrared transmitters in the structured electromagnetic radiation sensor, detect the coded signals at a set of infrared receivers, determine a set of time-of-flight values of the coded signals, and determine the distance or determine whether the eye is able to focus the image from the display monitor based on a difference between the set of time-of-flight values, and wherein the adjustable lens comprises a piezoelectric actuator around a flexible lens, and wherein the instructions further cause the processor to activate the piezoelectric actuator to expand or contract an outer perimeter of the flexible lens to adjust the optical power of the adjustable lens.

9. A method for displaying images, comprising:

disposing an adjustable lens arrangement on a line of sight between the display monitor and an eye of a user, the adjustable lens arrangement including one or more flexible lenses and one or more actuators;

collecting with a sensor arrangement, configurable to be optically coupled to the eye of the user, sensor data for determining at least one of a distance between a display monitor and the eye of the user or whether the eye of the user is able to focus on images displayed on the display monitor; and controlling with a focus arrangement, communicatively coupled to the adjustable lens arrangement and the sensor arrangement, the one or more actuators to adjust flexing of the flexible lens to adjust an optical power of the adjustable lens arrangement such that images projected on the display monitor are in focus for the eye of the user.

10. The method according to claim 9, wherein collecting with the sensor arrangement comprises collecting, with a sensor arrangement having a structured electromagnetic radiation sensor arrangement, electromagnetic radiation sensor data for determining a diopter correction, based on the structured electromagnetic radiation sensor data collected.

11. The method according to claim 10, wherein the structured electromagnetic radiation sensor arrangement comprises a set of electromagnetic radiation transmitters and a set of electromagnetic radiation receivers; and wherein the method further comprises transmitting with the set of electromagnetic radiation transmitters, coded signals from the set of electromagnetic radiation transmitters onto the eye or a retina of the user; sensing reflections of the coded signals with the set of electromagnetic radiation receivers;

determining a time-of-flight for each of the coded signals;

determining, using the times-of-flights, at least one of measure a distance between the transmitter and the eye or retina of the user or whether the reflections are in focus based on a difference between the times-of-flights; and controlling with the focus arrangement, the one or more actuators to adjust flexing of the flexible lens to adjust the optical power of the adjustable lens arrangement, based on the distance or whether the reflections are in focus.

12. The method according to claim 11, further comprising the transmitters and receivers of the structured electromagnetic radiation sensor arrangement in the display monitor.

13. The method according to claim 9, wherein the one or more actuators comprise a plurality of piezoelectric actuators radially disposed around one of the flexible lenses; and wherein the method further comprises activating the piezoelectric actuators to expand or contract an outer perimeter of the flexible lens to adjust the optical power of the adjustable lens arrangement.

14. The method according to claim 9, wherein the images are virtual reality display images.

15. The method of claim 11, wherein the transmitting and receiving comprises transmitting and receiving with infrared (IR) transmitters and receivers.

16. The method of claim 15, wherein the IR transmitters comprise three IR transmitters arranged in a first triangular shape, wherein the IR receiver comprises three IR receivers arranged in a second triangular shape, wherein the first and second triangular shapes are geometrically similar shapes, wherein the first and second triangular shapes are proximate at an equivalent vertex in each triangular shape, and wherein the first and second triangular shapes are arranged in a mirror-image pattern.

17. The method of claim 11, wherein the sensor arrangement further comprises a moveable mirror, movable into or out of a path between the eye of the user and the display monitor, and wherein transmitting with the electromagnetic radiation transmitters comprises transmitting the coded signals onto the moveable mirror, and reflected onto the eye or a retina of the user, when the moveable mirror is moved into the path between the eye of the user and the display monitor.

18. The method of claim 17, wherein the focus arrangement is disposed in an apparatus having a support computer, including a processor; and wherein the method further comprises operating focus sensor logic with the processor to control and move the moveable mirror into or out of a path between the eye of the user and the display monitor.

19. The method of claim 11, wherein the focus arrangement is part of a support computer having a processor; and wherein the method further comprises operating focus sensor logic with the processor to control the one or more actuators to adjust flexing of the flexible lens to adjust the optical power of the adjustable lens arrangement, based on the distance or whether the reflections are in focus.

20. The method of claim 9, wherein the focus arrangement is part of a support computer having a processor; and the method further comprises operating with the processor to control the one or more actuators to adjust flexing of the flexible lens to adjust the optical power of the adjustable lens arrangement, such that images projected on the display monitor are in focus for the eye of the user of the apparatus.

21. The method of claim 9, wherein the disposing, collecting and controlling are performed for a head mount device.

* * * * *